United States Patent [19]

Hatfield et al.

[11] Patent Number: 5,234,827
[45] Date of Patent: Aug. 10, 1993

[54] ENZYMATIC PROCESS FOR MANUFACTURING FORMALDEHYDE AND HYDROGEN PEROXIDE

[75] Inventors: G. Wesley Hatfield, Corona del Mar; Dane A. Holberg, San Clemente, both of Calif.

[73] Assignee: Knobbe, Martens, Olson & Bear, Newport Beach, Calif.

[21] Appl. No.: 47,658

[22] Filed: May 8, 1987

Related U.S. Application Data

[63] Continuation-in-part of Ser. No. 825,856, Feb. 4, 1986, Pat. No. 4,920,055.

[51] Int. Cl.$^5$ .......................... C12P 7/24; C12N 9/04; C12N 1/14
[52] U.S. Cl. ..................... 435/147; 435/190; 435/818; 435/930; 435/938
[58] Field of Search ............... 435/147, 190, 818, 930, 435/938

[56] References Cited

U.S. PATENT DOCUMENTS

| | | | |
|---|---|---|---|
| 3,880,739 | 4/1975 | Leavitt | 195/28 |
| 4,202,941 | 5/1980 | Teranda et al. | 435/190 |
| 4,353,987 | 10/1982 | Wolfe | 435/147 |
| 4,540,668 | 9/1985 | Hopkins | 435/190 |

OTHER PUBLICATIONS

Tani et al., "The Microbial Metabolism of Methanol", *Agr. Biol. Chem.*, vol. 36, No. 1, pp. 76–83, 1972.
Sahm and Wagner, "Microbial Assimilation of Methanol", *Eur. J. Biochem.*, vol. 36, pp. 250–256, 1973.
Ellis et al., "Isolation of Alcohol Oxidase and Two Other Methanol Regulatable Genes from Yeast *Pichia pastoris*", *Molecular and Cellular Biology*, vol. 5, No. 5, pp. 1111–1121, May 1985.
Levine and Cooney, "Isolation and Characterization of a Thermotolerant Methanol-Utilizing Yeast", *Applied Microbiology*, vol. 26, No. 6, Dec. 1973, pp. 982–990.
Van Dijken et al., "Growth of *Hansenula polymorpha* in a Methanol-Limited Chemostat", *Arch. Microbiol.*, vol. 111, pp. 137–144, 1976.
Baratti et al., "Preparation and Properties of Immobilized Methanol Oxidase", *Biotechnology and Bioengineering*, vol. XX, pp. 333–348, 1978.
Couderc and Baratti, "Immobilized Yeast Cells with Methanol Oxidase Activity: Preparation and Enzymatic Properties", *Biotechnology and Bioengineering*, vol. XXII, pp. 1155–1173, 1980.
Bock and Frieden, "Another Look At The Cold Lability of Enzymes", *TIBS*, vol. 3, No. 5, pp. 100–103, May 1978.
Griep et al., "Possible Basis for the Apparent Surface Selectivity of the Contact Activation Human Blood Coagulation Factor XII", *Biochemistry*, vol. 25, pp. 6688–6694, 1986.
Isohashi et al., "A Cold-Liabile Acetyl-Coenzyme-A Hydrolase from the Supernatant Fraction of Rat Liver", *Biochem.*, vol. 142, pp. 177–181, 1984.
Somero, "Temperature As a Selective Factor in Protein Evolution: The Adaptational Strategy of Compromise", *J. Exp. Zool.*, vol. 194, pp. 175–188.
Ledeboer et al., "Molecular Cloning and Characterization of A Gene Coding for Methanol Oxidase in *Hansenula polymorpha*", *Nucleic Acids Research*, vol. 13, No. 9, 1985.
Kato et al., "Enzyme System for Methanol Oxidation in Yeasts", *Arg. Biol. Chem.*, vol. 38, No. 3, pp. 675–677, 1974.

(List continued on next page.)

Primary Examiner—Elizabeth C. Weimar
Assistant Examiner—P. R. Moody
Attorney, Agent, or Firm—Knobbe, Martens, Olson & Bear

[57] ABSTRACT

A process is disclosed for enzymatically converting lower alkyl alcohols to corresponding aldehydes and hydrogen peroxide in the presence of oxygen under process conditions which increase the catalytic capacity of alcohol oxidase enzymes. Such process conditions involve low temperatures, high substrate concentrations and an enriched supply of oxygen. Enzymes may be used in the form of whole cells, a soluble cell free extract or a highly purified fraction, and the process may be employed in batch or continuous operation.

23 Claims, 2 Drawing Sheets

OTHER PUBLICATIONS

Patel et al., "Microbial Oxidation of Methanol: Properties of Crystallized Alcohol Oxidase From a Yeast, Pichia sp", *Archives of Biochemistry and Biophysics*, vol. 210, No. 2, pp. 481–488, Sep. 1981.

Geissler et al., "Flavin-dependent Alcohol Oxidase From Yeast", *Eur. J. Biochem.*, vol. 160, pp. 93–100, 1986.

Geissler and Hemmerich, "Yeast Methanol Oxidases: An Unusual Type of Flavoprotein", *FEBS Letters*, vol. 126, No. 2, pp. 152–156, Apr. 1981.

Mincey et al., "Presence of a Flavin Semiquinone In Methanol Oxidase", *Proc. Nat. Acad. Sci. U.S.A.*, vol. 77, No. 12, pp. 7099–7101, Dec. 1980.

Sherry and Abeles, "Mechanism of Action of Methanol Oxidase, Reconstitution of Methanol Oxidase With 5-Deazaflavin, and Inactivation of Methanol Oxidase by Cyclopropanol", *Biochemistry*, vol. 24, No. 11, pp. 2594–2605, 1985.

Bravo and Wang, "Enzymatic Oxidation of Methanol To Produce For Formaldehyde And Hydrogen Peroxide", *Adv. Biotech.*, vol. 3, pp. 329–334, 1981.

Roggenkamp et al., "Biosynthesis and Regulation of the Peroxisomal Methanol Oxidase From the Methylotrophic Yeast *Hansenula polymorpha*", *Mol. Gen. Genet.*, vol. 194, pp. 489–493, 1984.

Ribbons, "Oxidation of $C_1$ Compounds by Particulate Fractions From *Methylococcus capsulatus*: Distribution and Properties of Methane-Dependent Reduced Nicotinamide Adenine Dinucleotide Oxidase (Methane Hydroxylase)", *Journal of Bacteriology*, vol. 122, No. 3, pp. 1351–1363, Jun. 1975.

Luck, "Catalase", *Section C: Measurement of Enzyme Activity*.

Bjurstrom, "Biotechnology", *Chemical Engineering*, pp. 126–158, Feb. 18, 1985.

Tani et al., J. Ferment. Technol., 63(5), pp. 443–450, (1985), Biol. Abst. 81:52205.

Couperg et al., Agricultural and Biological Chemistry, 44(10), pp. 2279–2289, (1980).

ENZYMATIC PROCESS FOR MANUFACTURING FORMALDEHYDE AND HYDROGEN PEROXIDE

RELATED APPLICATION

This is a continuation-in-part of U.S. application Ser. No. 825,856, filed Feb. 4, 1986, now U.S. Pat. No. 4,920,055.

BACKGROUND OF THE INVENTION

This invention relates to a process which increases the catalytic capacity of alcohol oxidases (EC 1.3.13). These enzymes occur in a number of micro-organisms, acting to convert a lower alkyl alcohol, such as methanol or ethanol, to a lower alkyl aldehyde, such as formaldehyde or acetaldehyde and hydrogen peroxide in the presence of oxygen. The use of alcohol oxidase enzymes to manufacture commercially important chemicals from inexpensive feedstocks provides an alternative which could be economically superior to the synthetic processes now in use.

An enzyme suitable for commercial processes should be cheap and productive. An organism able to use an inexpensive feedstock and in which the alcohol oxidase can be induced to very high levels would obviously provide an economical source of enzyme. Such an enzyme must further satisfy productivity criteria. Specifically, it must tolerate high concentrations of substrates and products and have a high catalytic capacity, an ability to convert a relatively high amount of substrate to products before inactivation. Catalytic capacity is defined as the ratio of two rate constants, the first determined by the rate at which the enzyme converts substrate into product, having a constant, $K_{cat}$, and the second determined by the rate at which the enzyme becomes inactivated by product, having a constant, $K_{inact}$:

$$\frac{K_{cat}}{K_{inact}} = \text{catalytic capacity.}$$

Accordingly, high catalytic capacity can be achieved by increasing the specific activity of the enzyme (S.A.=umoles/min/mg enzyme) and/or extending enzyme half-life ($t_{\frac{1}{2}}$).

The prior art has focused on the identification of a suitable organism and alcohol oxidase enzyme, and has particularly focused on yeasts (organisms which are common to the fermentation art), e.g., Kloeckera Sp. No. 2201 (Tani et al., Agr. Biol. Chem. 36, 76-83 [1972]) Candida Boidinii (Sahm and Wagner, European J. Biochem, 36, 250-256 [1973]), and Pischia pastoris. (Ellis, et al., Mol. Cell Biol. 5, 1111-1121 [1985]). Another such organism is Hansenula polymorpha. The first step in the methanol utilization mechanism of these organisms is the aerobic oxidation of methanol into formaldehyde and hydrogen peroxide.

$$CH_3OH + O_2 \rightarrow HCHO + H_2O_2$$

In the in vivo system, the resulting hydrogen peroxide is rapidly decomposed by a catalase into oxygen and water. Levine and Cooney, Appl. Microbiol. 26(6), 982-990 (1973) isolated from soil a strain of Hansenula polymorpha, designated DL-1 (ATCC 26012) in which the methanol utilizing enzyme was thermotolerant (up to 50° C. for free cells) and therefore compatible with conventional fermentation conditions. Van Dijken, et al., Arch. Microbiol. 111, 137 (1976) reported that this enzyme can be induced to a level of 20% of total soluble cell protein in Hansenula polymorpha.

Barratti, et al., Biotechnology and Bioengineering 20, 333-388 (1978), using cell-free extracts of Hansenula polymorpha DL-1, found that although conversion yields were excellent (98%), the methanol oxidizing enzyme had limited substrate tolerance (100 mM or about 0.04% methanol) and that at high concentrations of enzyme, dissolved oxygen became rate-limiting. Later, Couderc and Barratti, Biotechnology and Bioengineering 22, 1155-1173 (1980), developed techniques to increase the substrate tolerance of the enzyme in cells to 500 mM at the expense of conversion yield, and noted that the enzyme was inhibited at low levels of the product, $H_2O_2$.

The inventors have found that enzyme from Hansenula polymorpha ATCC 34438 is relatively free from the potentially limiting factor of inactivation by feedstock concentration and inhibition by product concentration. Moreover, this strain of Hansenula, when grown under methanol limited conditions, could produce enzyme in a concentration of at least 20% of a cell-free extract, thus providing a relatively concentrated source of enzyme without extensive purification.

When reaction conditions were optimized within the conventional range, the inventors found that this alcohol oxidase was able to produce formaldehyde and hydrogen peroxide under conditions of higher product and feedstock concentrations, representing more than an order of magnitude improvement over the prior art.

It is well established that the properties of enzymes are affected by temperature. Although many proteins are stabilized somewhat by lowering the temperature below 25° C., others exhibit cold lability. Bock, et al., TIBS 3, 100-103 (1978). Temperature changes often change the conformation of an enzyme, which in turn may affect enzyme properties in what is still a relatively unpredictable manner. See, e.g., Griep, et al., Biochemistry 25, 6688-94 (1986) (factor XII activation optimized at low temperatures); Isohashi, et al., Eur. J. Biochem. 142 (1984) (acetyl-CoA hydrolase inactivated at low temperature); Somero, J. Exp. Zool. 194, 175-88 (1975) (review of temperature effects on enzymes).

The present invention employs radical reaction conditions of low temperatures and high feedstock concentration to increase the catalytic capacity of certain alcohol oxidase enzymes from Hansenula and Pischia at least sixty-fold and encompasses the discovery that this surprising and unexpected result extends to analogous systems using alcohol oxidases from related organisms.

Accordingly, it is an object of the invention to provide a process for the enzymatic conversion of alcohol to aldehyde and hydrogen peroxide that increases the catalytic capacity of these enzymes to a commercially viable level.

BRIEF DESCRIPTION OF THE INVENTION

We have discovered that under conditions of low temperature and high substrate concentrations, the catalytic capacity of alcohol oxidase enzymes, such as the enzyme from a strain of Hansenula polymorpha, having American Type Culture Collection (ATCC) Accession No. 34438, and Pischia pastoris, (commercially available from Provesta Corporation, Bartlesville, Okla., USA) can be extended to meet the requirements of a commercially feasible process for the conversion of alcohol to both aldehyde and hydrogen peroxide. The shift in reaction conditions can result in at least a sixty-fold increase in catalytic capacity with a relatively smaller decrease in reaction velocity over the prior art.

Thus, in accordance with one aspect of the present invention there is disclosed a process for the enzymatic conversion of alcohol to both aldehyde and hydrogen peroxide comprising the steps of contacting an aqueous solution of lower alkyl or lower alkenyl alcohol (i.e., having five or fewer carbon atoms), preferably methanol, ethanol or allyl alcohol, with an alcohol oxidase to convert the alcohol to aldehyde and hydrogen peroxide, while maintaining the temperature of the reaction mixture below about 10° C.

In accordance with preferred embodiments of the present invention the running temperature of the reaction mixture is maintained at about 5° to 10° C. above the calculated or measured freezing point of the reaction mixture. Accordingly, the temperature of the reaction mixture is maintained below about 5° C. and above the determined freezing point of the reaction mixture, preferably below about −0° C. or −5° C. and above the determined freezing point of the mixture, and most preferably below about −10° C. or −15° C. and above the determined freezing point of the mixture. In another preferred embodiment of the present invention the aqueous feedstock solution of alcohol is at least 4% by volume, preferably at least 15% or 20% by volume, and most preferably at least 25% or 30% by volume.

In accordance with preferred embodiments of the invention, the methanol oxidase enzyme is derived from a strain of yeast cells, preferably from a strain of Hansenula, Pischia, Candida, or Torulopsis and most preferably from *Pischia pastoris* or *Hansenula polymorpha* ATCC 34438.

One process for converting alcohol to aldehyde within the scope of the present invention comprises the use of an alcohol oxidase enzyme in the form of a soluble cell-free extract. Another process within the scope of the present invention utilizes alcohol oxidase as a constituent of a preparation of whole cells wherein the cell membranes have been ruptured either by freeze-thawing or by osmotic or mechanical means.

Another process within the scope of the invention utilizes alcohol oxidase as a constituent of a preparation of yeast cells wherein the cytoplasmic membrane walls have been disrupted by the action of a detergent.

In accordance with another preferred embodiment of the invention, the process for the conversion of alcohol to both aldehyde and hydrogen peroxide includes the step of adding oxygen or an oxygen-containing gas to the reaction mixture. Oxygen or an oxygen-containing gas is preferably added to the reaction mixture at a concentration or pressure sufficient to raise $O_2$ concentration of the liquid to 0.8 mmolar.

In accordance with ye another aspect of the present invention, the above process may be used to convert particular lower allyl and lower alkenyl alcohols to their respective aldehydes and hydrogen peroxide. Examples are the conversion of ethanol to acetaldehyde and hydrogen peroxide, the conversion of methanol to formaldehyde and hydrogen peroxide, and the conversion of allyl alcohol to acrolein and hydrogen peroxide.

DETAILED DESCRIPTION OF THE PREFERRED EMBODIMENTS

By carrying out enzymatic reactions of methanol oxidase at temperatures below about 10° C. and at substrate concentrations up to 30% or greater, the catalytic capacity and the product yield of the enzyme are substantially and surprisingly increased. The process finds particular application in the use of such enzymes in commercial procedures to synthesize aldehydes and hydrogen peroxide from lower alcohols.

Yeasts in the genera Pischia, Candida, Torulopsis, and Hansenula possess a methanol utilizing pathway which involves the fixation of formaldehyde (derived from methanol) to xylulose-5-phosphate, the conversion of that product into dihydroxyacetone and glyceraldehyde-3-phosphate, and the eventual regeneration of xylulose-5-phosphate. It appears that all alcohol oxidase enzymes from organisms that use this pathway may be used in the present invention. The steps of the reaction are carried out in the subcellular peroxisomes. The first step of that pathway involves the oxidation of methanol to formaldehyde and hydrogen peroxide and is catalyzed by alcohol oxidase. (The literature refers to this enzyme both as alcohol oxidase and methanol oxidase. As used herein, these terms are considered to be synonymous.) This alcohol oxidase in *Hansenula polymorpha* is an octamer of identical subunits with a molecular weight of 70,050, giving a total molecular weight for the enzyme of 560,400. The expression of genes coding for alcohol oxidase and the other enzymes involved in the metabolism of methanol is subject to glucose repression. In the presence of methanol, alcohol oxidase is induced to a high level in the cell, comprising as much as 20% of the protein of the soluble content of the cell. Alcohol oxidases using the xylulose-5-phosphate pathway are attractive for commercial utilization because they contain an auto-oxidizable cofactor as part of the enzyme complex (FAD) and because, unlike many other bacterial and yeast alcohol oxidases, they do not require a readily dissociable cofactor such as NAD which must be regenerated by additional enzymatic or chemical reactions.

The preferred alcohol oxidases are functionally identical to the alcohol oxidases derived from the strain of *Hansenula polymorpha* available from the American type Culture Collection, 13021 Parklawn Drive, Rockville, Md., U.S.A. ("ATCC") under accession No. 34438 and from *Pischia pastoris*. The base sequence of the alcohol oxidase gene for *Hansenula polymorpha* ATCC 34438 and the amino acid sequence for the subunits making up this enzyme have been identified for this strain. See Ledeboer et al. (1985) Nuc. Acids Res. 9, 3063-3082, which is hereby incorporated by reference. Other alcohol oxidases that may be used include those from *Hansenula polymorpha* DL-1 ATCC 26012, *Candida boidinii*, and Torulopsis. Appropriate screening procedures for enzyme activity, catalytic capacity at low temperatures and product tolerance will be apparent from the disclosures that follow, and should be used to select alcohol oxidase enzymes having optimal properties.

The present process, using the preferred alcohol oxidases, is able to convert methanol (as well as other alcohols) to aldehydes and hydrogen peroxide in concentrations of methanol of at least 2%, 3% or 4%, preferably at least 10% or 15%, more preferably at least 25% or 30%, and most preferably at least 40% or 50%. The process is operable under conditions wherein the amount of water in the reaction mixture is very low., accordingly, the process can be used in reaction mixtures having methanol concentrations up to 90%, preferably up to 70%, more preferably up to 50% by volume.

The process is operable also under conditions of high product concentration. It can be used in concentrations of hydrogen peroxide of at least 0.5%, and preferably at least 1%, 2%, 3%, 4%, or 5% by volume; it can be used in concentrations of formaldehyde of at least 1% and preferably at least 2%, 3% or 4%, 5% or 6% by volume.

The process can be used at temperatures maintained below about 10° C., preferably below about 5° C. or 0° C., more preferably below about −5° C., and most preferably below about −15° C. or −20° C. The process can be used at temperatures down to a lower limit of about −40° C. or −50° C., depending on the freezing point of the alcohol-water mixture. It can be used over a broad pH range from 6.0 to 9.0, preferably at pH 6.0 to 7.0 for temperatures below 10° C. The process can be applied to a batch operation or to a continuous operation wherein the reaction products are continuously removed; it can be applied to reaction systems which are pressurized with an oxygen-containing gas or supplied with oxygen-enriched gas at atmospheric pressure. The supply of oxygen can be rate-limiting and reaction conditions are optimum at an $O_2$ concentration of 0.8 mM. At air saturation, a liquid will have an oxygen concentration of 0.2 mM. Since oxygen dissolves in liquid in proportion to its pressure in the gas phase, its concentration in liquid may be increased by enriching the oxygen content in the reaction atmosphere, or by increasing the pressure over the reaction mixture, or both, to increase oxygen content four-fold. The oxygen-containing gas may be bubbled through or perfused into the reaction mixture and it may also be recirculated.

The alcohol oxidase enzyme can be used in the highly purified state, or in the form of a soluble cell-free extract or a crude whole cell preparation from *Hansenula polymorpha*. Since alcohol oxidase can be induced to very high levels in the organism, and there are no purification losses, crude whole cell preparations are advantageous. However, the cells also contain catalase, an enzyme which catalyzes the dissociation of hydrogen peroxide to water and oxygen, and hydrogen peroxide production is inversely proportion to catalase activity. One means to reduce catalase activity takes advantage of the rapid decay of catalase. Crude alcohol oxidase stored at 4° C. for several days will be substantially depleted of active catalase enzyme. Barratti, et al. Biotechnology and Bioengineering 20, 333–338 (1978). Depletion may be monitored by means of an assay for catalase activity. Moreover, catalase function appears to be inhibited under the reaction conditions of the presently-disclosed process.

Alternatively, catalase activity can be substantially eliminated by increasing the pH of a crude cell extract or other catalase-containing composition to at least about 8.5 or 9.0 for a period of time sufficient to inactivate the catalase. At pH 8.5 or 9.0, the time required for catalase inactivation is about 6–10 hours. At pH 10 or above, catalase inactivation occurs within about 1–2 hours. The alcohol oxidase enzyme, in contrast to catalase, is resistant to inactivation at high pH.

Insoluble crude cell preparations are advantageous because they conveniently segregate the enzyme from its reaction products. "Activated" cells, having increased efficiency of interaction between substrate and enzyme, can be produced by partially disrupting the cell membrane through such methods as mechanical shearing, freeze-thaw, osmotic rupture or a detergent treatment to produce a "leaky" cell membrane. The strong cationic agent cetyl trimethyl ammonium bromide (CTAB) is an appropriate detergent. Thus, for example, cells may be treated for about 5 minutes in a solution of 0.02% to 0.2% CTAB, and washed several times in potassium phosphate buffer before being used for the enzyme reaction. Alcohol oxidase enzyme may also be used as a soluble cell-free extract. The use of soluble cell free extracts avoids purification losses and provides an enzyme preparation that can be uniformly dispersed in the reaction mixture. Highly purified enzyme may be prepared according to conventional enzyme purification procedures in order to produce catalase-free alcohol oxidase of high specific activity. Purified enzyme is used to determine specific activity or other enzyme parameters as part of the process of screening for suitable cell strains.

A. Preparation of Enzyme

The alcohol oxidase enzyme may be produced by transcription and translation of an appropriate gene, such as a *Hansenula polymorpha* gene that has been cloned and amplified by genetic engineering techniques. However, the preferred technique is simply the growth of *Hansenula polymorpha* and the induction of alcohol oxidase synthesis in that organism.

(1) Growth of *Hansenula polymorpha* and Enzyme Induction

Growth media for yeast are well known in the art. *Hansenula polymorpha* and other similar organisms may be grown in either a glucose or a methanol medium. A suitable glucose medium may contain, by weight, 0.4% $NH_4Cl$, 0.1% $KH_2PO_4$, 0.1% $K_2HPO_4$, 0.05%, $MgSO_4$·$7H_2O$, 0.05% yeast extract, and 1% glucose. A suitable methanol medium would contain the same nitrogen, potassium, phosphate, and sulfate sources, together with from 0.3% to 3% by volume methanol.

The growth rates of the yeast on glucose and on methanol are similar. The cell doubling time in glucose is somewhat less than 12 hours. The cell doubling time in methanol is slightly more than 12 hours. When the yeast is grown in a glucose medium, alcohol oxidase production is induced by diluting the yeast 1:10 from the glucose medium into a 3% by volume methanol medium and growing to late log phase, approximately 24 hours at 28° C.

Alternatively, yeast may be grown in a methanollimited chemostat in accordance with the method of Van Dijken, et al., Arch. Microbiol. 111, 137–144 (1976).

In the presence of methanol, the resulting *Hansenula polymorpha* contains at least 20% of the protein of a cell-free extract in the form of alcohol oxidase.

(2) Enzyme Purification

In the first step of a suitable enzyme purification procedure, the cells are disrupted and homogenized. A phosphate buffer may be used to adjust the pH prior to homogenization to about 7.5. After cell disruption, cell debris can be removed by centrifugation. The supernatant solution represents a cell-free enzyme extract.

A particularly preferred purification technique utilizes an ion exchange column to purify alcohol oxidase from the crude cell-free extract. This purification procedure is a relatively fast, inexpensive, and efficient method for producing large quantities of protein in a short period of time. The protein that elutes from a DEAE-cellulose column, for example, is free of cellular catalase. The alcohol oxidase from *Hansenula polymorpha* elutes from the DEAE-cellulose, using a salt-gradient elution, at approximately 0.3 M NaCl. At this stage the enzyme is approximately 80–90% pure. It is also possible to shorten this procedure further by eluting alcohol oxidase from the column using a batchwise elution rather than a salt gradient. The enzyme will be of a lower purity, but since the only contaminant that substantially affects the reaction is catalase (which catalyzes the reaction $2H_2O_2 \rightarrow 2H_2O$) and since catalase does not bind to the DEAE-cellulose under the conditions used, the extraneous contamination will be of little consequence. Residual catalase may be determined by appropriate assay. See, e.g., Luck, H., Methods of Enzymatic Analysis 885–894 (H. Bergemeyer ed. 1963).

One example of an effective ion-exchange purification technique is set forth in Example 1, below.

Example 1: Enzyme Purification

*Hansenula polymorpha* cells are collected by centrifugation (5,000 x g, 10 min.) and resuspended in 50 mM potassium phosphate buffer, pH 7 5 (using a ratio of cells:buffer of approximately 1:2). Cells are disrupted in a "Beadbeater" homogenizer for 3 min. total (6 bursts of 30 sec. with 5 min. cooling intervals on ice). The extract is centrifuged for 20 min. at 16,000 x g, 4° C, and the supernatant solution is applied to a DEAE-cellulose column which has been equilibrated with 50 mM potassium phosphate buffer, pH 7.5. The column is washed with 50 mM potassium phosphate buffer, pH 7.5, until all unabsorbed proteins are washed from the column. Alcohol oxidase is eluted from the DEAE-cellulose with a linear salt gradient from 0–0.6 M NaCl in 50 mM potassium phosphate buffer pH 7.5. Fractions containing alcohol oxidase are pooled and concentrated by vacuum dialysis. Purification data are set forth in Table 1.

ity) is assayed for its activity in the presence of high concentrations of methanol, i.e., 1% 2%, 5%, 7% and 10% by volume. It is also assayed for its activity in the presence of high concentrations of products, hydrogen peroxide and formaldehyde.

(1) Assays

Hydrogen peroxide assay: Hydrogen peroxide is assayed using peroxidase. The 1 ml reaction mixture contains: 25 ug peroxidase, 1 mM ABTS (2,2'-azino-di-[3-ethylbenzthioazoline sulphate-6]), 5.3 mM $CH_3OH$, 100 uM potassium phosphate buffer pH 7.5, and alcohol oxidase. To assay added hydrogen peroxide, hydrogen peroxide solutions are added to the reaction mixture, and $CH_3OH$ and alcohol oxidase are not included in these reaction mixtures. The reaction mixtures are incubated at 37° C. for 30 min. Reactions are stopped by the addition of 67 ul of 4 M HCl and are read at 410 nm. Concentrations of hydrogen peroxide are determined by comparison to a standard curve (1 $O.D._{410} = 18.5$ nmoles $H_2O_2$/ml).

Formaldehyde assay: Formaldehyde is assayed using Nash reagent (2 M Ammonium acetate, 50 mM acetic acid, 20 mM acetyl acetate). One part formaldehyde solution is mixed with one part Nash reagent and incubated at 37° C. for 30 min. At the end of the incubation period the reactions are read at 412 nm. Concentrations of formaldehyde are determined by comparison to a standard curve (1 $O.D._{412} = 248$ nmoles $CH_2O$/ml).

These assays were used for determining enzyme activity and/or levels of hydrogen peroxide and formaldehyde produced. Since ABTS acts to increase the enzyme activity, specific activity was calculated based either on the formaldehyde assay or on assays in which the enzyme had been inactivated by acid before adding ABTS.

C. Process Conditions for Oxidation of Lower Alkyl Alcohols

The enzyme retains activity over a pH range of from 6.5 to 9.0 under standard assay conditions at 37° C. The preferred process pH at reduced temperature is from 6.0 to 7.0, and a pH of 6.5 is particularly preferred. In certain processes, it may be desirable to use a relatively volatile buffer, such as $NH_4HCO_3$, which can be removed from product by distillation in the purification step.

TABLE 1

PURIFICATION OF ALCOHOL OXIDASE FROM HANSENULA POLYMORPHA

| Step | Volume (ml) | Protein (mg/ml) | Total Protein (mg) | Activity (umol/min/ml) | Total Activity (umol/min) | Specific Activity (umol/$H_2O_2$ min/mg) |
|---|---|---|---|---|---|---|
| Extract | 67 | 2.1 | 141 | 8.6 | 578 | 4.1 |
| DEAE cellulose | 130 | 0.26 | 34 | 43 | 553 | 16.5 |
| Vacuum dialysis | 8.0 | 3.5 | 28 | 58.3 | 466 | 16.6 |

The purity of the enzyme produced in Example 1 is determined by SDS-polyacrylamide gel electrophoresis. The alcohol oxidase remaining after the final $(NH_4)_2SO_4$ precipitation step has a purity greater than 95%.

B. Enzyme Properties

To screen for alcohol oxidase activity suitable for use in the process of the present invention, the purified enzyme (purified to at least to be free of catalase activ- The preferred buffers are phosphate and carbonate or bicarbonate buffers, including potassium phosphate, sodium bicarbonate, and ammonium bicarbonate, all adjusted to about pH 6.5.

Although the preferred alcohol oxidase enzyme exhibits its highest affinity for methanol, it also has a significant degree of activity on other lower alkyl and lower alkylene alcohols. Straight chain alcohols of four or fewer carbon atoms are particularly preferred. Aside from methanol, the enzyme exhibits greatest activity with ethanol and allyl alcohol, converting them, respectively, of acetaldehyde and acrolein. The specificity of Hansenula polymorpha ATCC 34438 alcohol oxidase to various substrates at 37° C. is set forth in Table 2

TABLE 2

SUBSTRATE SPECIFICITY OF ALCOHOL OXIDASE

| Substrate | Relative Activity |
|---|---|
| Methanol | 100 |
| Ethanol | 75 |
| n-Propanol | 25 |
| Isopropanol | 5 |
| n-Butanol | 15 |
| Isobutanol | 0 |
| n-Amylalcohol | 5 |
| Isoamylalcohol | 0 |
| n-Hexanol | 0 |
| Allylalcohol | 65 |
| Glycerol | 0 |
| Ethylene Glycol | 5 |

Alcohol oxidase has a low affinity for its substrates, (Km methanol, 2.0 mM; Km oxygen, 0.4 mM), and the rate of product formation has been shown to increase significantly when either methanol or oxygen or both are in excess (see: Van Dijken et al., Arch. Microbiol., 111, 137 (1976)). Because methanol is infinitely soluble in water, its excess is easily achieved. The concentration of oxygen at air saturation (0.2 mM), however, is rate limiting. Under conditions of excess methanol, 0.8 mM to 1.0 mM oxygen is required for the enzyme to approach maximum velocity. Correlation between enzyme velocity and enzyme concentration is therefore improved by increasing the partial pressure of oxygen in the reaction environment. Under the combination of low temperature and increase methanol concentration, the solubility of oxygen in the mixture is improved.

D. Enzyme Performance Under Conditions of Low Temperature and High Substrate Concentration The preferred alcohol oxidase from Hansenula polymorpha ATCC 34438 exhibits increased catalytic capacity under conditions of decreased temperature and increased methanol concentration. At low enzyme concentration (0.055 ug/ml) and air saturation of oxygen where product accumulation is less than 0.003%, catalytic capacity of the enzyme at −15° C. and 30% methanol is greatly increased over that at 37° C. and 40 mM methanol. A sixty-fold increase in catalytic capacity was accomplished with a fifteen-fold decrease in reaction velocity. Conditions of low temperature and increased methanol concentration similarly extend the catalytic capacity of commercially available yeast alcohol oxidase from Pischia pastoris in a parallel manner. Pischia pastoris alcohol oxidase is obtained from Provesta Corporation, Bartlesville, Okla.

Example 2: Catalytic Capacity and Substrate Concentration

A. Catalytic capacity was determined as total accumulated product using 0.055 ug/ml purified enzyme having a specific activity (S.A.) of 7.4 umoles/min/mg enzyme at 37° C, air saturation. Product levels were determined according to the assay procedures for formaldehyde and hydrogen peroxide described herein.

(1) Alcohol oxidase was incubated at 37° C. in 0.5 ml of 0.1 potassium phosphate buffer, pH 7.5, at a methanol concentration of 40 mM. Aliquots were removed at selected times and assayed for product concentration. Catalytic capacity was calculated as $3.1 \times 10^5$ moles of hydrogen peroxide and formaldehyde formed/mole of enzyme active site, or 18.8 g of hydrogen peroxide per g of enzymes. The measured half-life of the enzyme was 1.2 h.

(2) A similar assay was carried out at −15° and 30% methanol. Catalytic capacity was calculated as 1145 g hydrogen peroxide per g enzyme. The measured half-life of the enzyme was 50 days.

B. The catalytic capacity of alcohol oxidase in a range of substrate concentrations was determined for the temperature range of 5° C. to −15° C. at air saturation with 0.055 ug/ml enzyme. The results are graphically illustrated in FIG. 1, in which the ordinate is catalytic capacity and the abscissa is methanol concentration. As is graphically apparent from the data presented therein, catalytic capacity for any given temperature may be optimized by adjusting methanol concentration. To put it another way, each curve peaks at a particular methanol concentration which is different for each temperature. Data not included in FIG. 1 have shown that highest catalytic capacity is obtained at about −22° C. with a methanol concentration of about 50% (w/v).

During prolonged catalysis of methanol to formaldehyde and hydrogen peroxide, alcohol oxidase is progressively inactivated, resulting in a loss of catalytic capacity. This inactivation, which is independent of enzyme concentration, probably involves oxidation at or near the active site of the enzyme by newly synthesized product molecules. At high product levels and under standard conditions, the enzyme is also slowly inactivated by hydrogen peroxide and to a lesser extent by formaldehyde in the reaction mixture. At room temperature (25° C.), catalytically inactive enzyme (that is, enzyme in the absence of the substrates methanol and oxygen), was reduced in activity by 50% after 2 h incubation in 0.007% hydrogen peroxide or 0.002% formaldehyde. However, when alcohol oxidase is incubated at −20° C. and 50% methanol, product inactivation is substantially reduced.

Example 3: Catalysis at High Product Concentration

Alcohol oxidase was incubated at −15° C. and 30% methanol alternatively in the presence of either hydrogen peroxide or formaldehyde for several hours. Aliquots were removed at intervals and assayed for residual activity. Due to high endogenous product levels, the residual activity of the hydrogen peroxide incubation was assayed for formaldehyde production and that of the formaldehyde incubation assayed for hydrogen peroxide production. The results in Table 3 indicate that during the course of a six hour incubation period the enzyme retains over 80% of its activity at levels of 4% formaldehyde or 2% peroxide.

TABLE 3

Product Denaturation of Catalytically-Active Enzyme at Low Temperatures and High Methanol Concentration

| | Control | 2% $CH_2O$ | 4% $CH_2O$ | 1% $H_2O_2$ | 2% $H_2O_2$ |
|---|---|---|---|---|---|
| vo$H_2O_2$ | 17.0 | 17.8 | 14.31 | ND | ND |
| vo$CH_2O$ | 20.2 | ND | ND | 18.3 | 17.5 |

$v_o$ is initial velocity in moles/hr/ml., activity measured after incubation for 6 h with indicated % product, employing 0.22 mg/ml enzyme, 30% methanol, 80 psi O$_2$ at $-15°$ C.

Example 4: Continuous Conversion of Methanol to Formaldehyde and Hydrogen Peroxide In a continuous process for the conversion of methanol to formaldehyde and hydrogen peroxide, 10 l. 50% by volume aqueous methanol solution is added to a reaction vessel. The solution is adjusted to pH 6.5 and the temperature of the system is reduced to about $-22°$ C. and maintained continuously at that temperature. A quantity of alcohol oxidase enzyme is added to provide an enzyme concentration of about 0.2 mg/ml in the reaction vessel. The reaction vessel is pressurized with air to about 5 atmospheres, and the pressurized air is sparged through the mixture. Alternatively, 4 mmoles/min oxygen can be sparged through the mixture and pressurization of the vessel is optional. The gas is removed from the top of the reaction vessel. Air or oxygen is added to the recirculated gas in order to maintain excess oxygen in solution.

An ultrafiltration material having a molecular weight cut-off of about 100,000 is provided at the inlet and at the outlet of the reaction vessel. Methanol and water are continuously introduced into the reaction zone of the reactive mixture to maintain the methanol concentration at about 50%. The reaction products are continuously removed from the reaction vessel through the ultrafiltration material. The ultrafiltration material at the outlet of the reaction vessel is periodically back-flushed to remove enzyme accumulating thereon. That enzyme is then recirculated into the reaction vessel. Fresh enzyme is added to the reaction vessel to maintain the active enzyme concentration at approximately 0.2 mg/ml. The reaction mixture removed from the vessel contains approximately 4% formaldehyde, 4% hydrogen peroxide, and about 50% methanol, by volume.

E. Process Apparatus

Figure 2:
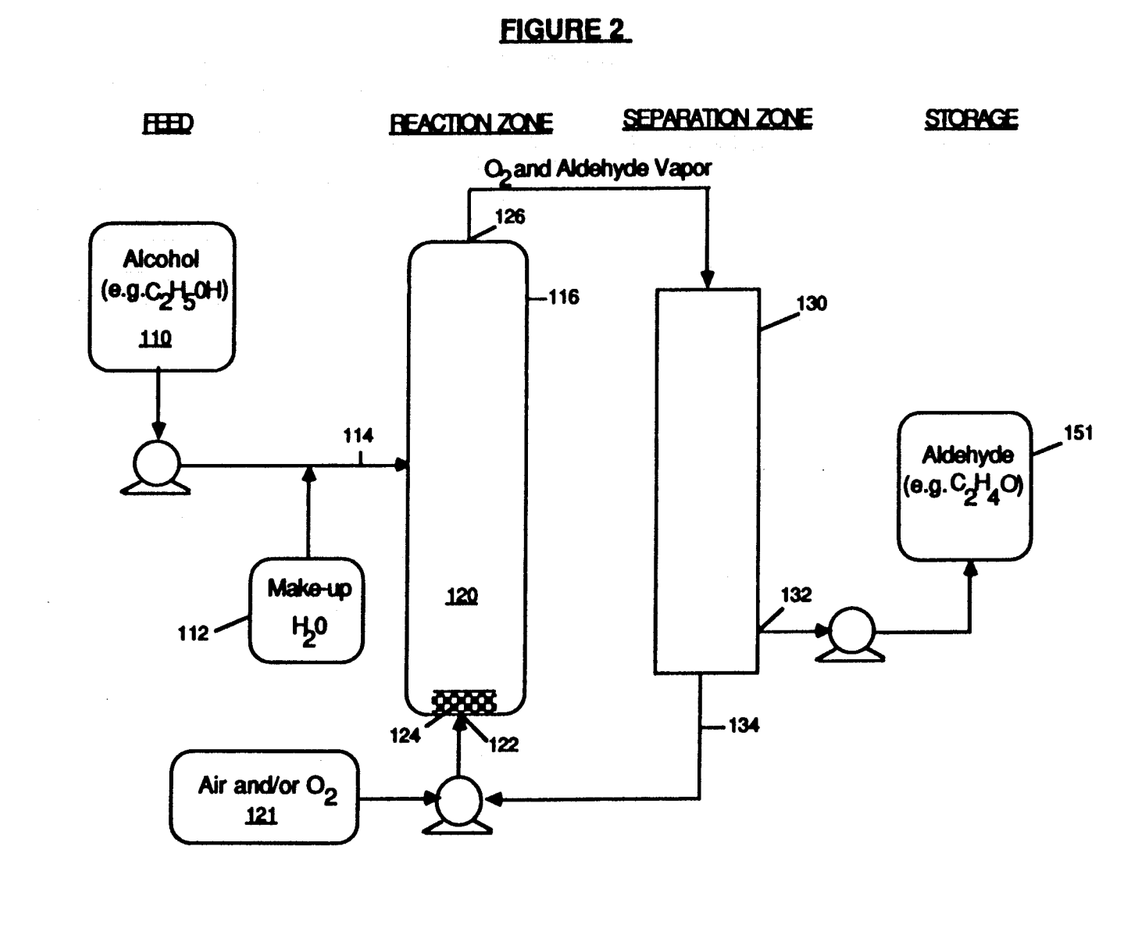
FIG. 2 is a schematic representation of an apparatus for the continuous or batchwise conversion of alcohol to aldehyde and hydrogen peroxide.

A suitable apparatus for the continuous-type conversion of alcohol into aldehyde and hydrogen peroxide in accordance with the present invention is shown schematically in FIG. 2. An alcohol source 10 and a water source 12 are provided. An inlet line 14 introduces alcohol and water into a reaction zone 16. In FIG. 2, the reaction zone 16 is preferably a refrigerated, pressured chamber or container or a plurality of chambers or containers. The reaction zone may alternatively comprise an elongated structure. One example of such a structure is a tube. The reaction zone 16 contains a reaction mixture 20. This reaction mixture contains water, alcohol that is introduced into the reaction zone through inlet line 14, alcohol oxidase enzyme, and oxygen. Due to the action of the alcohol oxidase enzyme on the alcohol, the reaction mixture 20 also contains aldehyde and hydrogen peroxide.

Means such as gas inlet 22 are provided for introducing an oxygen-containing gas from an oxygen source 21 into the reaction zone 16. This gas is preferably oxygen gas, O$_2$. The reaction zone 16 is ordinarily pressurized to increase the rate and degree of oxygen dissolving into the reaction mixture 20. The preferred oxygenation technique is a sparging technique. The reaction zone 16 may advantageously include porous material 24 or other conventional material for dispersing the oxygen as bubbles throughout the reaction zone 16. Gas is removed from the reaction zone 16 through the gas outlet 26. Means 30 for recirculating gas from the gas outlet 26 back to the gas inlet 22 may also be provided. Such a recirculating means 30 has the advantage of both conserving oxygen and reintroducing any vaporized aldehyde back into the reaction zone 16 and the reaction mixture 20. Recirculation also prevents expelling unhealthful products, such as formaldehyde, into the environment. Inside the reaction zone 16 or connected to the reaction zone 16 is preferably a means for agitating or mixing the reaction mixture 20. In FIG. 2, the agitation means is the porous material 24 and the oxygen-containing gas passing through the porous material 24 to form bubbles that continuously agitate and mix the reaction mixture 20 in the reaction zone 16.

The reaction zone 16 is bounded at its outlet 32 by an enzyme recovery means 34. The enzyme recovery means 34 may be a dialysis membrane or an ultrafiltration material. The enzyme recovery means 34 is capable of passing species of small molecular weight, such as aldehydes and hydrogen peroxide, while retaining high molecular weight species, particularly the alcohol oxidase enzyme used in the present invention, which has a molecular weight of 560,400. In order to prevent a flow-restricting accumulation of enzyme on the enzyme recovery means 34, the flow rate per unit area of the enzyme recovery means 34 is kept low. For any given throughput, this is done by making the semipermeable membrane very large or by utilization of a tangential flow membrane apparatus. Periodically, the enzyme recovery means may be washed to remove accumulated enzyme. This can be done by introducing a backflow of liquid through the enzyme recovery means 34 or by directing a liquid flow across, rather than through, the enzyme recovery means 34. Enzyme recovered from the enzyme recovery means 34 is recycled back into the reaction zone 16 through a line 36.

From the reaction zone 16, the aldehyde and hydrogen peroxide produced in the reaction zone pass through the outlet 32 and the enzyme recovery means 34 into a separation zone 40. The separate zone 40 may comprise a distillation apparatus for separating aldehyde from hydrogen peroxide. In practice, more volatile aldehydes can be separated from the hydrogen peroxide as a gaseous mixture. In the case of formaldehyde, this gaseous mixture also contains water and small quantities of methanol. In the case of formaldehyde no further purification will ordinarily be necessary, despite the presence of methanol and water in the end product in vessel 51, because formaldehyde is ordinarily sold as an aqueous solution and that aqueous solution is usually stabilized with small quantities of methanol.

In the separation step, the hydrogen peroxide is removed from the separation zone as an aqueous solution to storage vessel 52. Hydrogen peroxide is ordinarily sold as an aqueous solution but it also may be further concentrated using conventional techniques if desired. With suitable separation apparatus some water is recovered and reintroduced through recirculation line 41.

Figure 1:
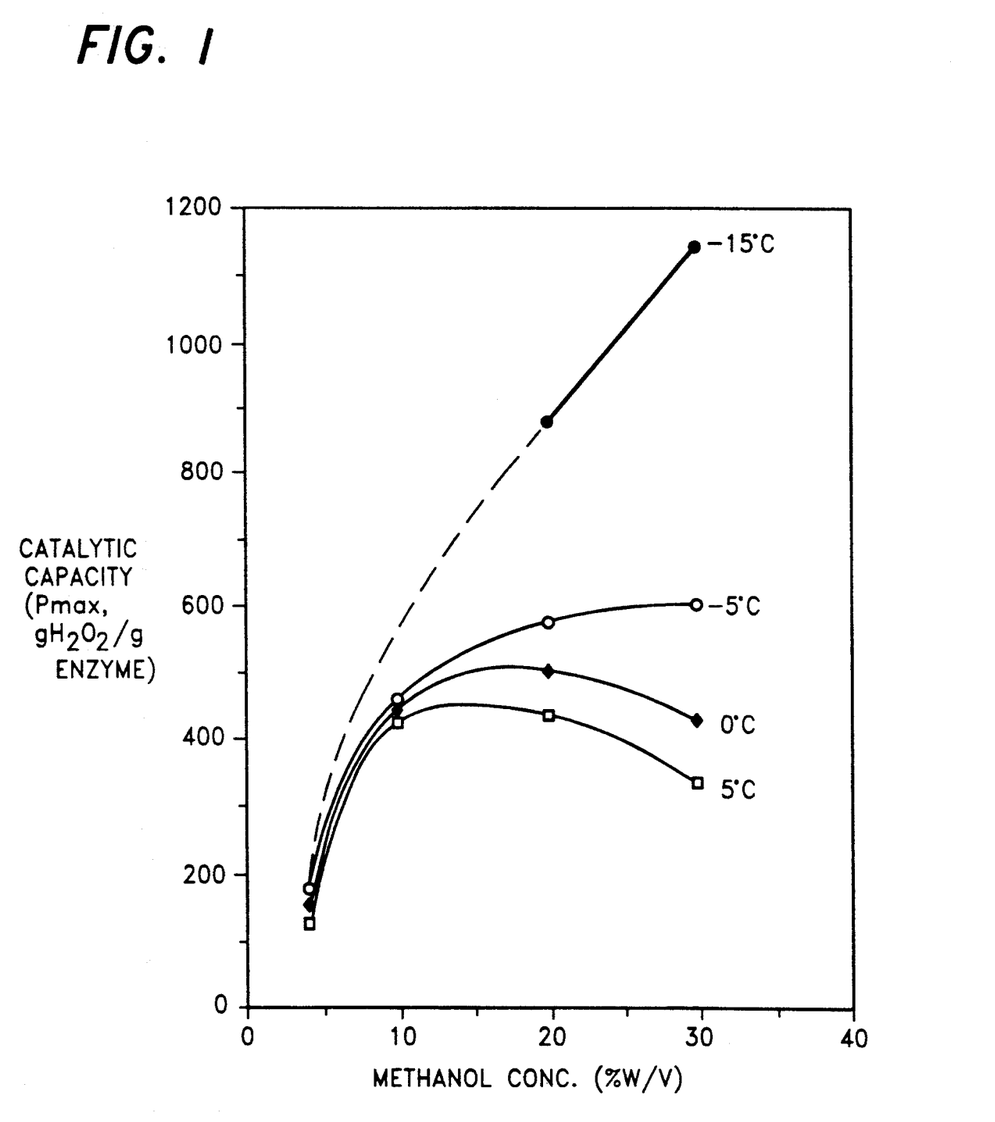
FIG. 1 is a plot of catalytic capacity versus methanol concentration at four different temperatures.

A batch-type process according to the present invention may also be practiced with the apparatus of FIG. 1. Water, alcohol, and enzyme are introduced into the refrigerated reaction zone 16 through inlet line 14 to form a reaction mixture 20 and to fill up the reaction zone 16 to the desired level. The reaction mixture 20 remains in the reaction zone 16, with an oxygenating gas being introduced into the reaction zone 16 through as inlet 22 and porous material 24. The gas is removed from gas outlet 26 and recirculated through recirculation means 30. The bubbling of the oxygen-containing gas through the reaction mixture 20 provides agitation and mixing so that the reaction mixture 20 is substantially homogeneous. When the reaction has gone to the desired stage of completion, reaction mixture 20 is removed from the reaction zone 16 through the outlet 32. The enzyme is removed from the reaction mixture 20 by the enzyme recovery means 34, and the reaction mixture proceeds into the separation zone 40. The reaction zone 16 may then be refilled with reaction mixture 20, and the process repeated.

In one example of a batch process using 50% methanol in water (w/v), 1.9 mg/ml crude Hansenula polymorpha ATCC 34438 extract, under 80 psi pure oxygen, the reaction mixture after 3.6 days at −22° C. contained 6.5% formaldehyde and 5.1% hydrogen peroxide. Extrapolated endpoint values for product are 7.7% formaldehyde and 6.9% hydrogen peroxide.

We claim:

1. A process for the enzymatic production of hydrogen peroxide in vitro, comprising the steps of:
   introducing water, lower alkyl alcohol or lower alkenyl alcohol, and extracellular alcohol oxidsase into a reaction zone to form a reaction mixture, wherein said reaction mixture is substantially free from catalase activity;
   maintaining the temperature of the reaction mixture below 0° C.; and
   enzymatically converting said alcohol in said reaction mixture into an aldehyde and hydrogen peroxide.

2. The process of claim 1, wherein the concentration of said alcohol is maintained at at least 10% weight/volume.

3. The process of claim 1, wherein the concentration of hydrogen peroxide in said reaction mixture after enzymatic conversion of said alcohol is permitted to reach at least about 0.5% weight/volume.

4. The process of claim 1, wherein said temperature is maintained below about −5° C. and above the freezing point of said reaction mixture.

5. The process of claim 1, wherein said temperature is maintained below about −10° C. and above the freezing point of said mixture.

6. The process of claim 1, wherein the concentration of said alcohol in said reaction mixture is at least 20%.

7. The process of claim 1, wherein the concentration of said alcohol in said reaction mixture is at least 25%.

8. The process of claim 1, wherein said temperature is below about −10° C. and said concentration of said alcohol is at least about 25% weight/volume.

9. The process of claim 1, 2, or 8, wherein said alcohol oxidase is derived from yeast cells.

10. The process of claim 9, wherein said alcohol oxidase is derived from *Hansenula polymorpha*.

11. The process of claim 10, wherein said alcohol oxidase is derived from *Hansenula polymorpha* ATCC 34438.

12. The process of claim 9, wherein said alcohol oxidase is derived from *Rischia pastoris*.

13. The process of claim 9, wherein said alcohol oxidase is in the form of a soluble cell-free extract.

14. The process of claim 13, in which said process includes the step of substantially eliminating catalase activity from said crude extract by increasing the pH of the crude extract to at least pH 8.5.

15. The process of claim 9, wherein said alcohol oxidase is a constituent of a preparation of ruptured cells.

16. The process of claim 9, wherein said alcohol oxidase is a constituent of a preparation of cells having cell membranes that have been disrupted by the action of a detergent.

17. The process of claim 1 or claim 2, wherein said reaction mixture is oxygenated by contacting at least some of the water in the reaction mixture with an oxygen-containing gas at a pressure greater than atmospheric.

18. The process of claim 1 or claim 2, wherein said reaction mixture is oxygenated by contacting at least some of the water in the reaction mixture with an oxygen-containing gas at a pressure greater than 2 atmospheres.

19. The process of claim 1 or 2, wherein said alcohol is methanol.

20. The process of claim 1 or 2, wherein said alcohol is ethanol.

21. The process of claim 1 or 2, wherein said alcohol is allyl alcohol.

22. The process of claim 1, wherein the concentration of hydrogen peroxide in said reaction mixture is permitted to reach at least about 1%, weight/volume.

23. The process of claim 1, wherein the concentration of hydrogen peroxide in said reaction mixture is permitted to reach at least about b 2%, weight/volume.

* * * * *